United States Patent [19]

Scales et al.

[11] Patent Number: 4,828,564
[45] Date of Patent: May 9, 1989

[54] ENDOPROSTHETIC BONE JOINT DEVICES

[75] Inventors: John T. Scales, Stanmore; William Bonfield, Welwyn; Keith W. J. Wright, Ruislip, all of England

[73] Assignee: National Research Development Corporation, London, England

[21] Appl. No.: 85,225

[22] Filed: Aug. 13, 1987

Related U.S. Application Data

[63] Continuation of Ser. No. 814,085, Dec. 24, 1985, abandoned, which is a continuation of Ser. No. 693,824, Jan. 23, 1985, abandoned, which is a continuation of Ser. No. 592,084, Mar. 22, 1984, abandoned.

[30] Foreign Application Priority Data

Mar. 22, 1983 [GB] United Kingdom ............... 8307820

[51] Int. Cl.$^4$ ........................... A61F 2/38; A61F 2/30
[52] U.S. Cl. ........................................ 623/20; 623/18
[58] Field of Search ....................... 623/16, 18, 20, 21, 623/22, 23

[56] References Cited

U.S. PATENT DOCUMENTS

| 2,785,673 | 3/1957 | Anderson | 623/23 |
| 3,848,272 | 11/1974 | Norles | 128/92 CA |
| 4,012,796 | 3/1977 | Weisman | 128/92 CA |
| 4,051,559 | 10/1977 | Pifferi | 3/1.912 |
| 4,064,568 | 12/1977 | Grundei et al. | 3/1.911 |

FOREIGN PATENT DOCUMENTS

| 0046926 | 3/1982 | European Pat. Off. | 623/20 |
| 1328497 | 8/1973 | United Kingdom . | |
| 2070939 | 9/1981 | United Kingdom | 623/18 |
| 2085461 | 4/1982 | United Kingdom | 3/1.9 |
| 83/02555 | 8/1983 | World Int. Prop. O. | 623/18 |

Primary Examiner—Richard J. Apley
Assistant Examiner—David J. Isabella
Attorney, Agent, or Firm—Cushman, Darby & Cushman

[57] ABSTRACT

A passively extensible long bone component in an endoprosthetic bone joint device for a child includes two parts, of which one (10,20) has a bearing portion (22) to serve the articulatory function at one end of the bone, a seat portion (11) to engage the bone one end proximally of the growth plate therein and a stem (21) to pass longitudinally into the bone, and of which the other part (30) is a generally tubular socket adapted to receive the stem in sliding engagement and for securement with the bone distally of the growth plate. The bearing part can be cushioned against shock, at least partially separable, and extend as a further socket between the first socket and the stem. The component can allow rotation of the bearing and stem about the bone long axis or inhibit such rotation.

3 Claims, 2 Drawing Sheets

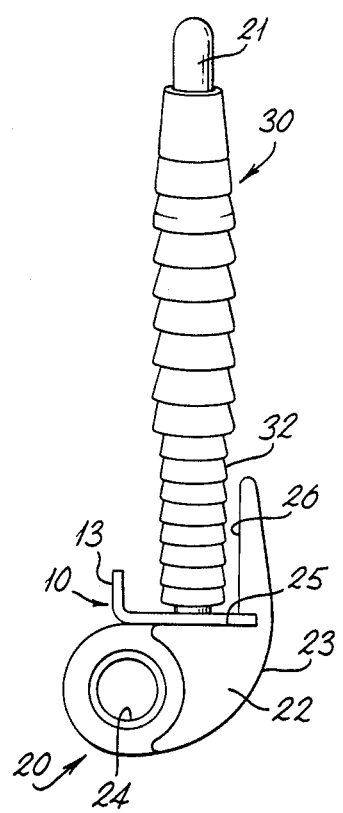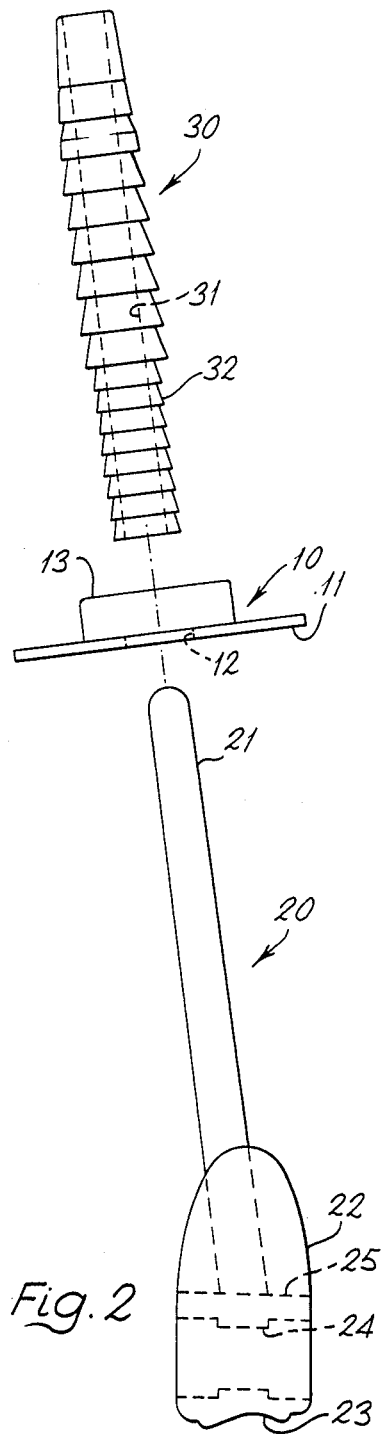
Fig.1
Fig.2

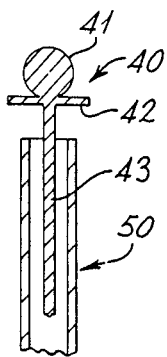 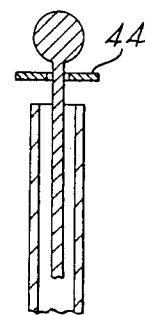
Fig. 3a.  Fig. 3b.
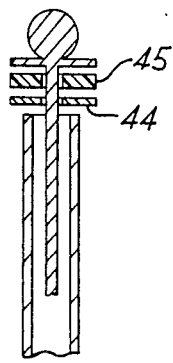 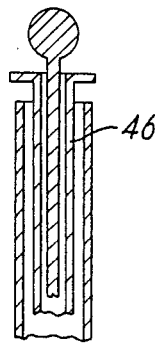 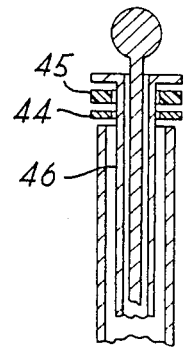
Fig. 3c.  Fig. 3d.  Fig. 3e.

ENDOPROSTHETIC BONE JOINT DEVICES

This is a continuation of application Ser. No. 814,085, filed Dec. 24, 1985, now abandoned, which was a continuation of Ser. No. 693,824, filed Jan. 23, 1985, which is a continuation of Ser. No. 592,084, filed Mar. 22, 1984, now abandoned.

This invention concerns endoprosthetic devices and more particularly such devices for use in children.

The use of an endoprosthetic bone joint device in a child is generally regarded as temporary. This view arises from two factors. Firstly, the joint will normally involve a long bone, and growth in a long bone is from its ends where a so-called growth plate of cartilagenic material progressively ossifies and moves on longitudinally until final coalescent ossification at maturity. Secondly, current designs of device commonly involve a component which seats on the end of the long bone and includes a stem which passes longitudinally into the bone for the purposes of component securement. Clearly, in application to a child, this component will pass through the growth plate with the result that continuing growth will act to move the component away from its securement and loosen the same.

The present invention seeks to improve this situation and to this end provides an endoprosthetic bone joint device comprising a component for a long bone and including two parts, of which one part seats on one end of the bone and has a stem to pass longitudinally into the bone, and of which the other part is in the general form of a tubular socket adapted to receive said stem in sliding engagement and for securement with the bone through the growth plate remotely from said one end on the other side of and beyond or behind the growth plate.

In application to a child the stemmed part of the component can move with growth of the bone end on which it is seated because it is not secured with the bone on the other side of the growth plate, but instead simply passes through this plate to be stabilised by its stem engagement in the secured socket.

The stabilisation will, of course, act to determine the longitudinal orientation and the transverse positioning of the stemmed part relative to the long bone. It can also serve to inhibit rotation of the stemmed part relative to the bone by the provision of keying between the stem and socket, or by non-circular transverse profiling of these parts. An alternative or additional mode of inhibiting rotation can involve the provision of a tab formation on that portion of the stemmed part which seats on the bone end, this formation serving to engage the side of the bone.

The stemmed part can vary in other respects than that just mentioned. This part will have three basic portions serving different functions. One portion is represented by the stem to afford stabilisation, another is a seat portion to engage with the bone end, and the third is a bearing portion to serve the relevant articulation function of the bone end. In one form of the invention all these portions are provided in a one-piece component part. In other forms these portions are at least partly separated in manufacture. The seat portion can be separate from the other two by provision as an apertured platform through which the stem portion passes and on which the bearing portion seats. Also such a seat portion can be extended as a further generally tubular socket slidably engaged in the first-mentioned socket and receiving the stem.

It will be noted that some of these forms allow stabilisation of the stemmed component part to the extent of inhibiting rotation of the seat portion relative to the bone end, but at the same time allow rotation of the bearing portion. This can be advantageous in affording improved simulation of natural articular movement and also in reducing the transmission of deleterious forces through the overall device.

Also some of these forms allow the incorporation of shock absorbing material in the seating portion.

Variation is also possible in respect of the socket part at least to the extent that adaption to different modes of securement can be deployed. Clearly use can be made of established securement techniques by the provision of screw threading, fins, or other formations to effect a direct mechanical lock in bone, and by the use of bone cement. However, it is presently considered that further development of the invention will involve securement techniques which rely at least partly on so-called ingrowth, and the use of material according to UK patent specification No. 2085461A is specifically contemplated for this purpose.

The invention may be clarified by the following description, given by way of example, of an early embodiment thereof and variations thereon as illustrated in the accompanying drawings, in which:

FIG. 1 shows the embodiment in assembled side view,

FIG. 2 shows the embodiment in exploded front view, and

FIG. 3 schematically illustrates some possible variations.

The illustrated embodiment is the femoral component for a knee joint device which accords generally with UK patent specification No. 1,328,497.

This component comprises three separate sub-components of which two, 10 and 20, together constitute the stemmed part referred to above, and the third one, 30, is the associated socket part.

The sub-component 10 is the seat portion and comprises a plate 11 shaped to represent the lower end of the femur in plan view. This plate has a central aperture 12 and a laterally elongated tab 13 projecting perpendicularly from its rear edge.

The sub-component 20 incorporates the stem and bearing portions of the component. The stem portion is constituted by a cylindrical member 21 rounded at its free end and projecting a its other from the bearing portion. The bearing portion is seen to comprise a generally L-shaped member 22 having its outer surface 23 longitudinally curved and grooved, and having a bore 24 passing between the sides of one arm of the L-shape. The inner surface 25 of this last-mentioned one arm is that from which the stem member 21 projects, in slightly laterally inclined manner, and the remaining inner surface is denoted as 26.

The sub-component 30 is a generally tubular member having a cylindrical bore 31 and annular teeth 32 formed around its outer surface over the length thereof, with such teeth becoming progressively coarser from one end to the other of the member.

In use of this embodiment the end of the femur at the knee joint is prepared by suitable shaping, without bone removal to the extent of the growth plate to any significant degree, and the medullary canal is bored. The sub-component member 30 is located in the canal bore to effect a force-fit by virtue of the teeth 32, the coarser teeth being entered first, and thereby to firmly secure the same on the other side of beyond or behind the growth plate from the bone end while allowing growth to continue longitudinally beyond the outer end of the member. Thereafter the sub-component 10 is located on the bone end with its tab 13 disposed at the rear. The sub-component 20 then has its stem passed through the aperture 12 to enter the canal bore, pass through the growth plate and engage the socket member bore until the bearing portion member 22 seats by way of its surface 25 on the plate 11 and the stem extends beyond the growth plate. This seating is effected with the non-bored arm of the bearing member 22 located to the front with the surface 26 engaging a concavely profiled edge of the plate 11, and also the bone.

It will be appreciated that, as the bone grows, the sub-components 10 and 20 can move correspondingly without disturbing the securement of the sub-component 30 beyond the growth plate.

It remains to note that this femoral knee component is intended to be used in association with a related tibial component with which articulatory engagement is effected by a hinge pin passing through bore 24 of the bearing member, while the longitudinally curved and grooved surface 23 of the femoral component articulates mutually with the patella, as described in the above-mentioned specification No. 1,328,497.

Turning to FIG. 3: this schematically illustrates some possible variations which can be employed in application of the invention as already referred to in the introductory discussion above. There are five variations shown respectively as (a) to (e).

FIG. 3(a) can be regarded as showing the basic form of the invention to the extent that there are two separate parts 40 and 50. The first part 40 includes a bearing portion 41, a seat portion 42, and a stem 43, while the second part 50 is the socket. In practice this form will not normally allow rotation between the two parts and, for this purpose, the seat will be keyed with the bone and/or the stem will be keyed with the socket.

FIG. 3(b) shows a variation of (a) in which the seat portion is a separable washer-like element 44. In this case the seat should be keyed with the bone, while the stem can be keyed or rotatable in the socket. This variation is effectively that of FIGS. 1 and 2, and it is included at this point for completeness.

FIG. 3(c) can be viewed as combining (a) and (b) in that seats 42 and 44 are both used with a layer 45 of resilient shock-absorbing material therebetween, the seats themselves being of metal or other relatively non-resilient material. The layer 45 is shown, like seat 44, in washer form but the overall seat structure can, of course, be bonded together.

FIG. 3(d) is a variation on (b) in which the separable seat is extended into a further socket 46 slidably engaged in the first socket 50 and slidably receiving the stem. This variation is well suited to rotation of the bearing and stem relative to the bone and the remainder of the component.

Lastly FIG. 3(e) shows (d) further modified to incorporate a cushioned seat in the manner of (c).

Other variations are also possible in application of the invention. For example, specific reference has been made to a femoral component in a knee joint device and application can be equally appropriate to the related tibial component or long bone components in other joints such as the hip.

We claim:

1. The method of implanting an endoprosthetic bone joint component in an immature long bone, which component comprises two parts of which one includes a seat and a stem, and of which the other part defines a tubular socket for sliding receipt of said stem, such method comprising:
   preparing said bone at one end thereof for receipt of said component without removal of the growth plate at said bone one end;
   locating and securing said other part in said bone from said bone one end, but effecting such securement only beyond and behind the growth plate to allow continued growth of said bone without consequent disruption of said securement; and
   locating said one part by passing said stem into said bone one end through the growth plate to slidably engage said socket and to engage said seat against said bone one end, whereby said one part can move with continued growth of said bone while said stem continues to stabilize said one part.

2. The method of implanting an endoprosthetic bone joint component in an immature long bone, which component comprises an elongate tubular socket part, an apertured seat part, and an articulatory part including a bearing portion and a stem projecting therefrom, and which method comprises:
   preparing said bone at one end thereof for receipt of said component without removal of the growth plate at said bone one end;
   locating and securing said socket part in said bone from said bone one end, but effecting such securement only remotely from said bone one end and beyond the growth plate to allow continued growth of said bone without consequent disruption of said securement;
   locating said seat part on said bone one end and coupling the same to inhibit mutual rotation therebetween; and
   locating said articulatory part to pass said stem through said seat part into longitudinal sliding engagement in said socket part beyond the growth plate and to engage said bearing portion on said seat part remotely from said socket part, whereby said seat and articulatory part can move with continued growth of said bone while said stem continues to stabilize said articulatory part.

3. The method according to claim 2 which comprises coupling said bearing portion with said seat part to inhibit mutual rotation therebetween.

* * * * *